United States Patent [19]

Stanislas et al.

[11] Patent Number: 4,959,316
[45] Date of Patent: Sep. 25, 1990

[54] PROCESS FOR AMPLIFYING THE EXPRESSION OF A SPECIFIC GENE IN BACILLUS SUBTILIS, AND STRAINS OBTAINED

[75] Inventors: Ehrlich Stanislas, Paris; Janniere Laurent, Vitry sur Seine; Pierre Evelyne, Etrechy; Brigitte Niaudet, Paris, all of France

[73] Assignee: Centre National de la Recherche Scientifique (CNRS), Paris, France

[21] Appl. No.: 135,515

[22] Filed: Dec. 18, 1987

Related U.S. Application Data

[63] Continuation of Ser. No. 677,999, Dec. 4, 1984, abandoned.

[30] Foreign Application Priority Data

Apr. 27, 1984 [FR] France ................................. 84 6701

[51] Int. Cl.$^5$ ........................ C12N 15/00; C12N 1/00; C12N 1/20; C12P 21/00
[52] U.S. Cl. ................................. 435/172.3; 435/69.1; 435/71.2; 435/252.31; 435/832; 435/839; 935/42; 935/56; 935/74
[58] Field of Search ........................ 435/68, 70, 71, 91, 435/172.1, 172.3, 252.3, 252.31-252.35, 832, 839, 69.1, 71.2; 935/42, 55, 56, 74, 84

[56] References Cited

U.S. PATENT DOCUMENTS 4,336,336  6/1982  Silhavy et al. ..................... 435/172.3

FOREIGN PATENT DOCUMENTS 0074808  3/1983  European Pat. Off. ......... 435/172.3
2068971  8/1981  United Kingdom ............. 435/172.3
8400381  2/1984  World Int. Prop. O. ....... 435/172.3

OTHER PUBLICATIONS

Buchanan et al., (ed.), *Bergey's Manual of Determinative Bacteriology*, Eighth Edition, 1974, Williams & Wilkins Co., Baltimore, pp. 529–533.
Young, "Gene Amplification in *Bacillus Subtilis*: The Establishment of Multiple Tandemly-Repeated Copies of Heterologous DNA Segment in the Bacterial Chromosome", Chem. Abstr. 102: 198792a, (1985) of Genet. Biotechnol. Bacilli, Ganesan et al., (ed.), (1984).
Bonamy et al., "Cloning and Expression of *Bacillus Subtilis* Spore Genes", Molec. Gen. Genet. 188: 202 (1982).
Chem. Abstr. 102: 1392r (1985) of JP 59,151,889 (1984).
Saunders et al., "Use of Chromosomal Integration in the Establishment and Expression of blaZ, a Staphylococcus Aurea Beta-Lactamase Gene in *Bacillus Subtilis*", J. Bacteriol. 157: 718 (1984).
Duncan et al., "Mechanism for Integrating Foreign DNA during Transformation of *Bacillus Subtilis*", Proc. Natl. Acad. Sci., U.S.A., 75: 3664 (1978).
Galizzi et al., "Integration and Excision of a Plasmid in *Bacillus Subtilis*", Mol. Gen. Genet. 182: 99 (1981).
Williams et al., "Expression of *E. Coli* trp Genes Cloned in *B. Subtilis*", in *Molecular Cloning and Gene Regulation in Bacilli*, 1982, Ganesan et al., (ed.), Academic Press, New York, pp. 91–96.
Gaillard, Excision Sequences in the Mitochondrial Genome of Yeast, Nature, vol. 283, Jan., 1980, p. 218.

*Primary Examiner*—James Martinell
*Attorney, Agent, or Firm*—Wegner & Bretschneider

[57] ABSTRACT

The present invention relates to a process for preparing a strain of Bacillus, in the chromosome of which a specific gene has been amplified, in which process: (a) at least one plasmid integration vector bearing the said gene is integrated in the Bacillus chromosome so as to create in the chromosome: at least one DNA sequence, known as an amplifiable unit, which contains at least the said gene and its expression elements and, at each end, two sequences which are identical in the direct sense; the amplifiable unit which codes, furthermore, for a selectable gene; (b) the strains of Bacillus obtained are then selected by culture on a selection medium corresponding to the selectable gene, and the strains are withdrawn which have the phenotype corresponding to the presence of an increased number of copies of the said gene relative to the bacterial population before selection.

22 Claims, 7 Drawing Sheets

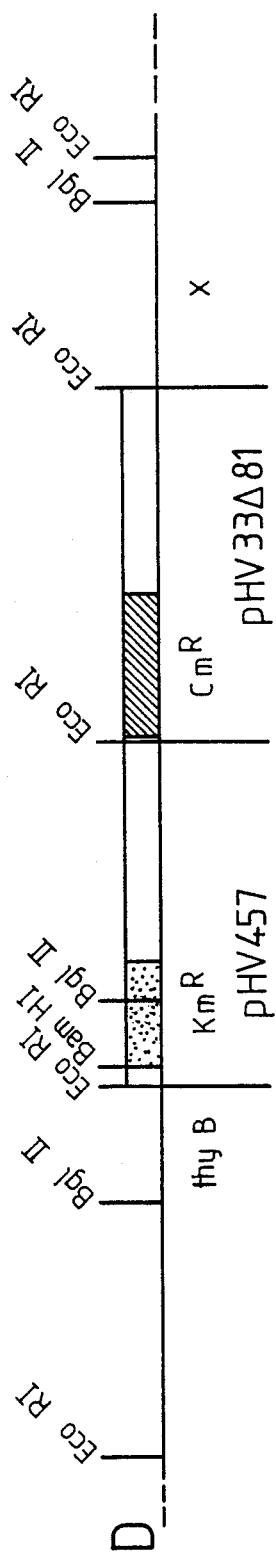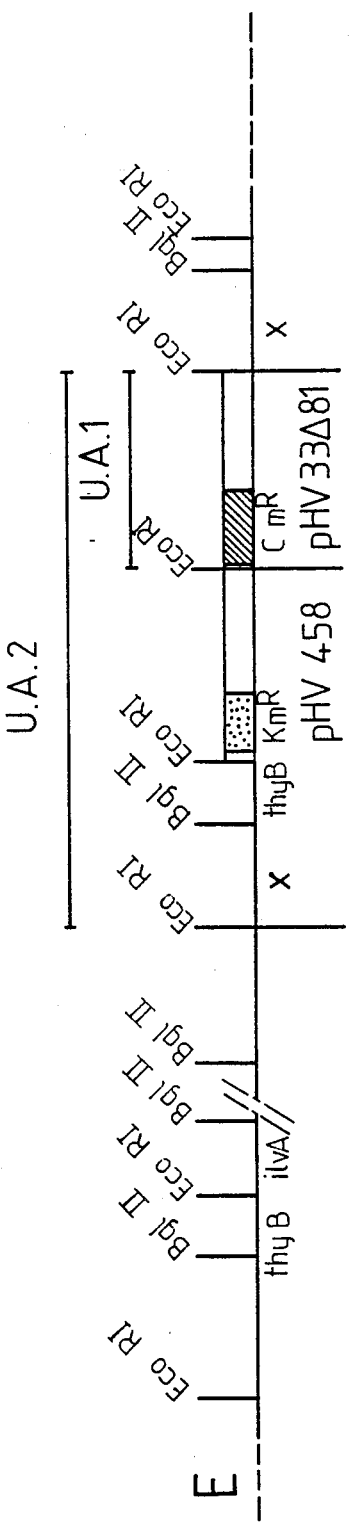

PROCESS FOR AMPLIFYING THE EXPRESSION OF A SPECIFIC GENE IN BACILLUS SUBTILIS, AND STRAINS OBTAINED

This application is a continuation of U.S. Ser. No. 677,999 (filed December 4, 1984), now abandoned.

The present invention relates to a process for amplifying the expression of a specific gene in Bacillus, in particular *B. subtilis*.

*B. subtilis* is currently a host of choice for the expression of foreign genes by techniques of genetic engineering, since this is a non-pathogenic bacterium for which the fermentation conditions at the industrial level are known.

For quite a long time, it has been possible to transform strains of *B. subtilis* by plasmid DNA, by using plasmids capable of replication.

However, there are difficulties linked to the instability of the hybrid plasmids in *B. subtilis*. At least two types of instability are defined:

the segregational instability associated with the total loss of plasmid by the host cell, and the structural instability associated with alterations in sequence, most frequently deletions.

These instability phenomena are much more common in *B. subtilis* than in *E. coli*, which explains in part why the latter bacterium is much more extensively used as host cell in current techniques.

This difficulty could be overcome if the clonal selection of foreign genes could be accomplished in the chromosome of *B. subtilis*, since in this case the stability is much greater. Integrating vectors have therefore been constructed for the purpose of integrating foreign genes into the *B. subtilis* chromosome. These vectors are mainly characterised by the presence of segments homologous with the chromosome of *B. subtilis*, which provide for the integration.

The integration of these vectors in the chromosome can, in outline, be accomplished according to the following two processes:

(1) By a recombination event involving a single crossing-over, described by Campbell (1962) (FIG. 1). This integration mechanism can only operate if the vector is recircularized in the receptor cell. This recircularization can arise either as a result of intramolecular recombination events if the vector is endowed with internal repetitions (Michel et al., 1982), or as a result of intermolecular recombination events with the homologous sequences present in the chromosome of the receptor cell (Niaudet et al., 1982). The vector can probably be recircularized by repairing the cleavage (as demonstrated for plasmids by Michel et al., 1982, 1983), using as a template homologous sequences carried by the vector itself, if it contains internal repetitions, or carried by the chromosome of the receptor cell. Integration by a Cambell type mechanism creates a duplication of the homologous sequences, which duplication encloses the foreign DNA (Haldenwang et al., 1980; Niaudet et al., 1982).

(2) By a mechanism of double crossing-over (FIG. 2). The linear vector must then have two regions of homology with the chromosomal DNA of *B. subtilis*, located on either side of the heterologous sequence (Harris-Warrick and Lederberg, 1977; Niaudet et al., 1982). If the two chromosomal segments carried by the vector are non-adjacent in the chromosome, the integration of the vector by double crossing-over leads to deletion of the chromosomal portion located between these two regions of homology (Niaudet et al., 1982).

This chromosomal integration in *B. subtilis* does not enable gene amplification to be obtained, as is the case with the self-replicating plasmid vectors. However, gene amplification is one of the conditions currently sought in the field of genetic engineering to provide for significant expression of the cloned gene and hence for the production of the corresponding proteins on the industrial scale.

The invention enables the disadvantages to be overcome by means of a process for preparing a strain of Bacillus, in the chromosome of which a specific gene has been amplified, in which process:

(a) at least one plasmid integration vector bearing the said gene is integrated in the Bacillus chromosome so as to create in the chromosome:

at least one DNA sequence, known as an amplifiable unit, which contains at least the said gene and its expression elements and, at each end, two sequences which are identical in the direct sense, the amplifiable unit which codes, furthermore, for a selectable gene;

(b) the strains of Bacillus obtained are then selected by culture on a selection medium corresponding to the selectable gene, and the strains are withdrawn which have the phenotype corresponding to the presence of an increased number of copies of the said gene relative to the bacterial population before selection.

The amplifiable unit preferably consists of an amplification unit which incorporates the said gene and its expression elements, the N-terminus of this sequence being identical to a sequence located after the amplification unit, these two identical sequences being referred to below as "duplicated sequences".

By means of this process, it is possible to select strains of *B. subtilis* which have undergone gene amplification at the chromosomal level both for the selection marker and for the specific gene, as will become clear on reading the examples.

In general, the selectable gene will be a gene for resistance to a chemical compound, in particular an antibiotic: kanamycin, chloramphenicol, ampicillin or tetracycline, for example.

Under these conditions, selection of the strain is simple, since it is sufficient to select a strain which is highly resistant to the antibiotic.

Thus, with an amplification unit containing, in addition to the duplicated sequence, the Km gene and, by way of specific gene, the Cm gene, it was possible to obtain gene amplification of Cm by selecting strains which were highly resistant to Km. This experiment shows clearly the value of the present invention if Cm is replaced by a gene coding for a protein of interest.

It is possible to obtain a strain which is hyperproductive of this protein and which is stable without there being the need to maintain selection pressure.

FIG. 3 shows, at the bottom, the schematic structure of a gene amplified by the process of the invention, starting from an amplifiable structure at the top which contains an amplification unit A.U. consisting of a duplicated sequence D and an amplified sequence M which contains the marker gene and the gene coding for the protein of interest.

From the technical standpoint, integration vectors are known as regards their basic principles and their particular embodiments.

As shown above, for integration to be capable of taking place, the vector needs to have a DNA sequence identical to that of the chromosome of the Bacillus strain. In some cases, vectors carrying fragments of the wild Bacillus chromosome are used, for example all or part of the thy B gene, or of a gene which will be called X. In other cases, a specific sequence originating, for example, from a bacterial plasmid such as pBR322 is previously introduced, and in this case it will be sufficient to use an integration vector carrying the same sequence. The latter technique is especially simple to carry out.

In general, the integration vector will contain an amplification unit consisting of a duplicated sequence, of a marker gene and of the specific gene, since the Bacillus chromosome contains a duplicated sequence before the integration.

The present invention also relates to strains of Bacillus, especially B. subtilis, obtained by carrying out the process of the invention, and also a process for culturing the strains obtained in order to prepare the product encoded by the specific gene.

Quite surprisingly, it was observed during the use of the strains according to the invention that the amplified structure was very stable, whereas it is usually accepted that such a structure is especially unstable whatever the bacterial species in which it has been obtained, and whatever its localization (chromosomal or plasmid). The process of the invention hence enables stable strains to be obtained which can be made use of industrially.

Other features and advantages of the present invention will emerge in the examples of embodiment below, which will be described with reference to the figures in which:

BRIEF DESCRIPTION OF THE DRAWINGS

FIG. 9 shows the structure of strain D, FIG. 10 shows the structure of strain E.

Except where otherwise indicated, the various enzymes are used according to the techniques recommended by the supplier.

(1) STUDY OF THE AMPLIFICATION OF THE GENE FOR RESISTANCE TO KANAMYCIN IN STRAIN A.

(1.1) Construction of strain A:

In order to study gene amplification, there is introduced in the B. subtilis chromosome a structure composed of a gene for resistance to kanamycin flanked by two identical sequences, in direct repetition, derived from pBR322 sequences.

Figure 4:
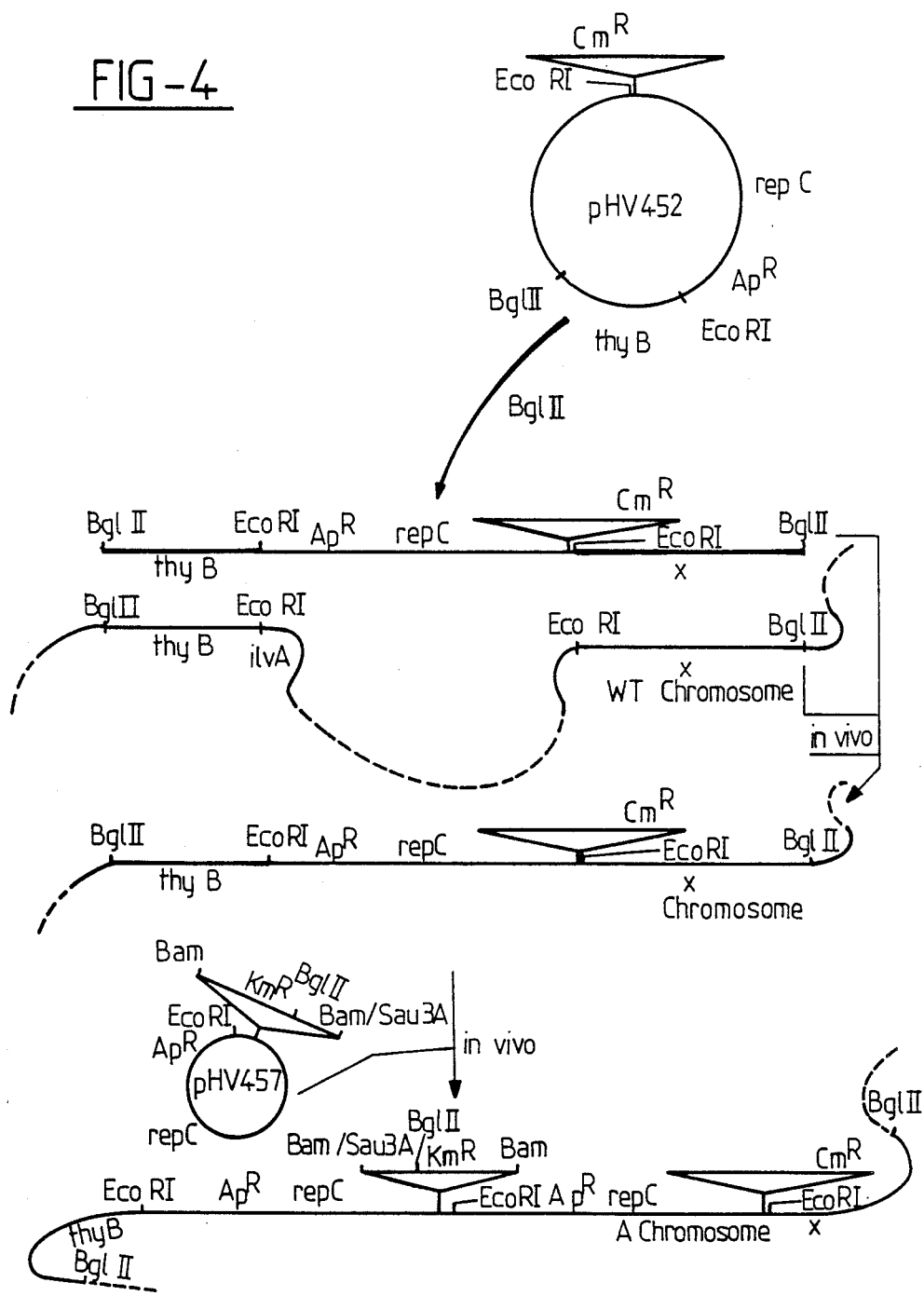
FIG. 4 shows the construction of strains α and A.

The strain containing this structure (called strain (A) was constructed in two stages:

(a) insertion of a first copy of pBR322 in the B. subtilis chromosome by a double crossing-over event (Niaudet et al., 1982) (production of strain α);

(b) insertion of the second copy of pBR322 and the Km gene by a Campbell type mechanism (production of strain A); the various stages of this construction are outlined in FIG. 4.

(a) Insertion of the first copy of pBR322 (strain α)

To insert the first copy of pBR322 in the B. subtilis chromosome, the integrating vector pHV452 is used. It is composed of two segments of the B. subtilis chromosome, one carrying the thy B gene (segment referred to as Thy B) and the other not containing a known function (segment referred to as X), and the E. coli plasmid pHV33Δ 81 (Dagert et al., 1984). pHV33Δ 81 is composed of the pC194 gene for resistance to chloramphenicol (Iordanescu, 1975) and pBR322 having part of the $Tc^R$ gene deleted. By means of these two chromosomal segments, pHV452 can be integrated in the B. subtilis chromosome and confer chloramphenicol resistance on the host bacterium.

pHV452 linearized by the endonuclease BglII was used to transform competent cells of B. subtilis strain SB202. $10^5$ $Cm^R$ transformants/μg of DNA were obtained. All the transformants were Ile⁻, which shows that linearized pHV452 was integrated in the B. subtilis chromosome following a double recombination event between the plasmid segments and the chromosomal segments Thy B and X (FIG. 4) (Niaudet et al., 1982). The original chromosomal region located between these segments, containing the ilvA gene, is then deleted and replaced by pHV33Δ 81, loss of the ilvA gene conferring the Ile⁻ phenotype on the strain (Barat et al., 1965).

Chromosomal analysis of an Ile⁻ $Cm^R$ transformant shows that the latter has the structure shown in FIG. 4. The strain thereby constructed hence contains a sequence derived from pBR322 inserted between the chromosomal regions Thy B and X.

(b) Insertion of the second copy of pBR322 and the $Km^R$ gene (strain A)

To construct a strain containing a duplication of the pBR322 sequences around the gene for kanamycin resistance, a plasmid composed of pBR322 sequences and the gene for kanamycin resistance was integrated in the pBR322 region of strain α by a Campbell type recombination event.

The plasmid used, pHV457, comprises the pBR322 sequences and the segments Sau3A I and IV and pUB110 (Staphylococcus aureus plasmid (Gryczan et Dubnau, 1978)). These segments, inserted in the BamHI site of pBR322, contain a gene for kanamycin resistance and a site for the restriction enzyme BglII (Michel et al., 1982) (FIG. 4).

Figure 1:
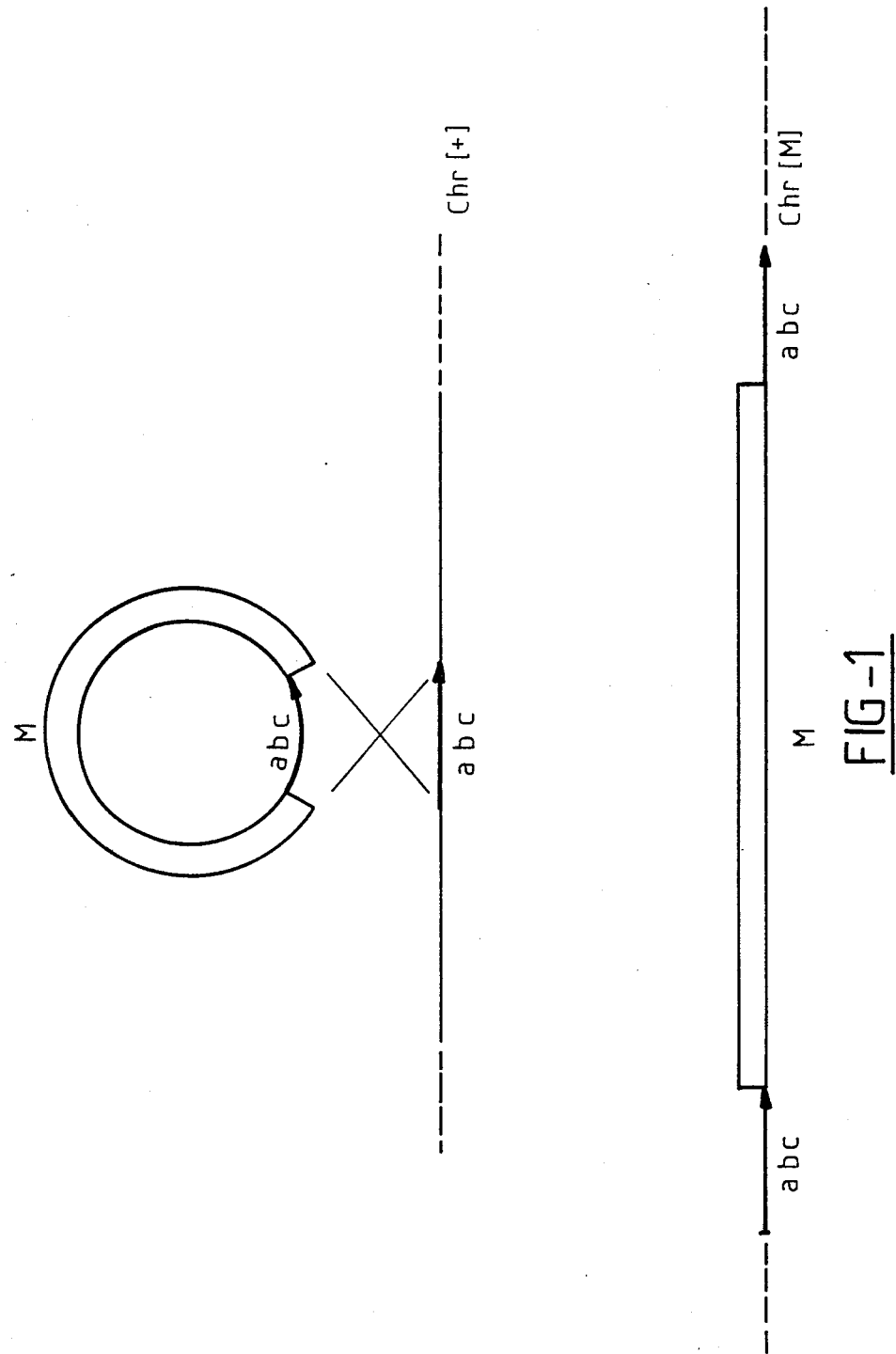
FIG. 1 shows a diagram of a single recombination event.
Figure 2:
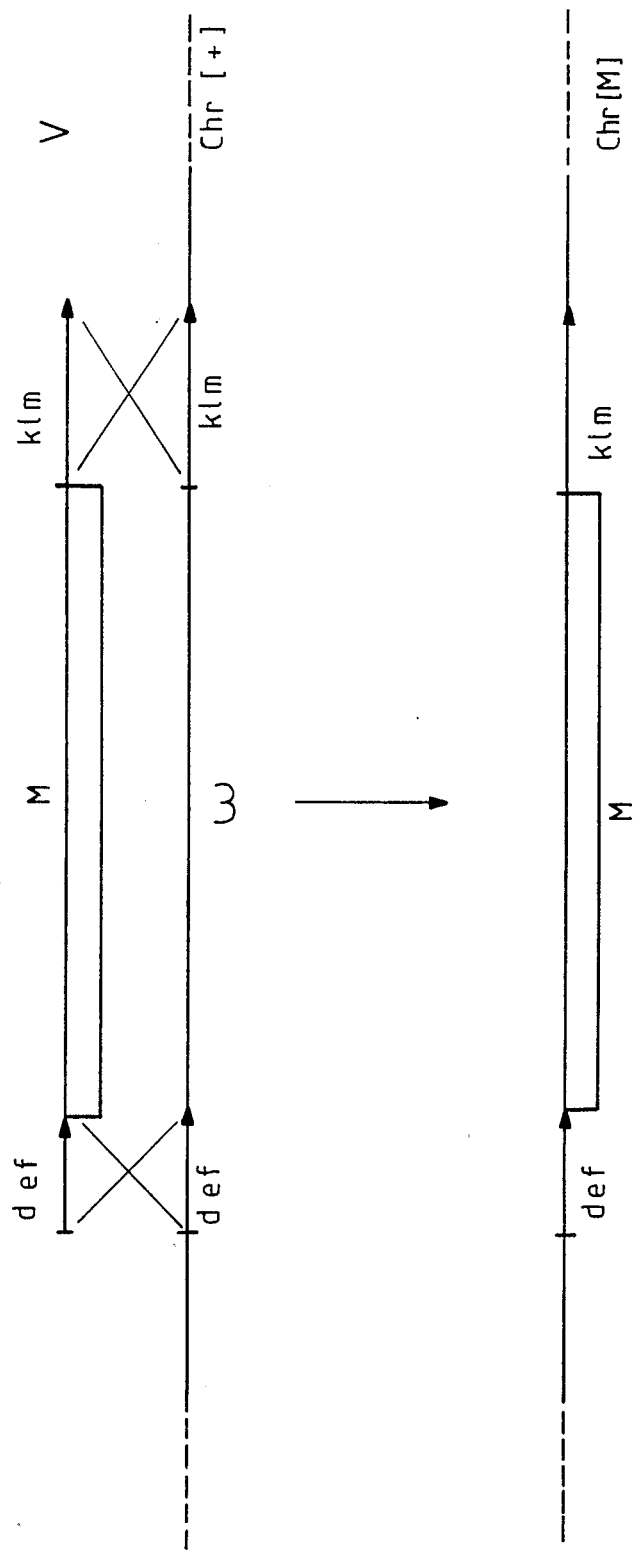
FIG. 2 shows a diagram of a double recombination event.
Figure 3:
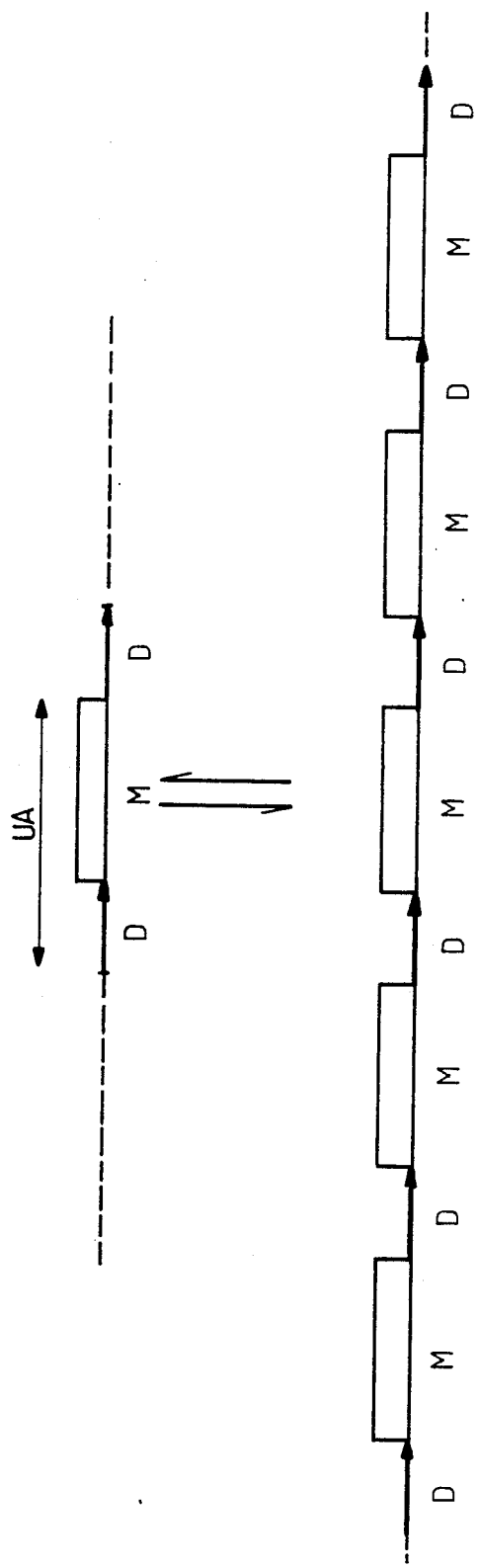
FIG. 3 shows a diagram of gene amplification.
Figure 5:
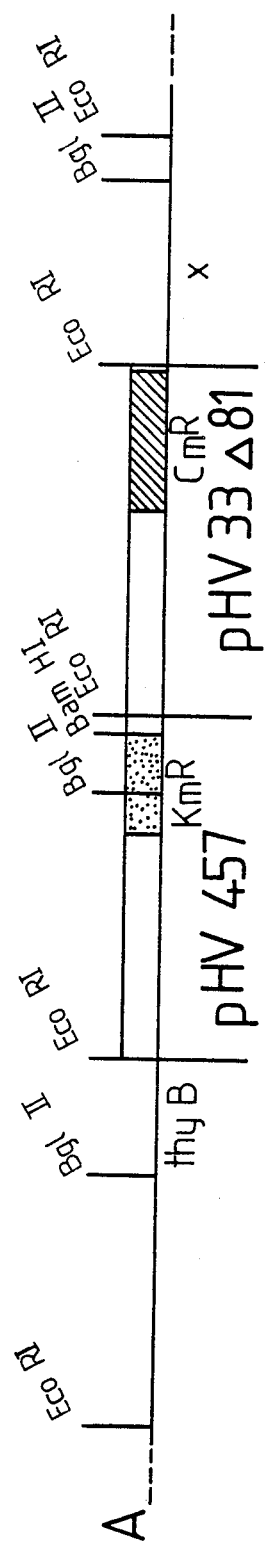
FIG. 5 shows the structure of strain A.

Since it was observed to be impossible to select the integration of a single copy of pHV457 in the B. subtilis chromosome, this plasmid was introduced into competent cells of strain SB202 (Trp⁻), in congression with the chromosomal DNA of strain HVS246 (Trp⁺). Among the Trp⁺ transformants obtained, 5% of the clones were resistant to kanamycin. The chromosomal DNA of a Trp⁺ $Km^R$ transformant was extracted and analyzed according to Southern's hybridization technique, after restriction with BglII or EcoRI using pHV33Δ 81 as a probe. The autoradiogram obtained shows that the transformant analyzed has the structure shown in FIGS. 4 and 5. Strain A thereby constructed hence contains in its chromosome an amplifiable structure where the gene for kanamycin resistance is flanked by two homologous sequences derived from pBR322. The amplification unit of strain A, as was defined in the description, is pHV457. It is important to note that this strain has never been in direct contact with kanamycin, the phenotype for kanamycin resistance being detected by means of a subculture of this strain.

(1.2) Detection of bacteria resistant to subinhibitory concentrations of kanamycin To investigate bacterial subpopulations in strain A resistant to concentrations of kanamycin greater than those tolerated by the population as a whole (sub-inhibitory concentrations), aliquots of a culture of strain A were plated on solid medium containing increasing concentrations of kanamycin.

The results show:

that a copy of the $Km^R$ gene confers resistance to 1 $\mu$g/ml of this antibiotic (the parent strain SB202, which does not contain this gene, is resistant to 0.5 $\mu$g/ml of kanamycin);

that there are bacteria in strain A resistant to concentrations of kanamycin greater than 1 $\mu$g/ml; the frequency of these bacteria varies from $10^{-4}$ to $5\times 10^{-7}$.

(1.3) Enrichment of bacteria resistant to kanamycin concentrations of 2 to 10 $\mu$g/ml Strain A was seeded in liquid medium (the initial concentration being $10^6$ cells/ml) containing increasing concentrations of kanamycin (1 to 10 $\mu$g/ml). Every hour, the optical density of these cultures was measured at 600 nm.

The results of this experiment show:

the existence of a spontaneous subpopulation resistant to 10 $\mu$g/ml of kanamycin (referred to as A $Km^R10$), having a frequency of $5\times 10^{-7}$. This subpopulation grows with a generation time of approximately 20 min. After 8 hours of culture, it becomes predominant.

By successive culture of strain A (equivalent to 30 cell generations) in liquid medium containing graded concentrations of kanamycin from 2 to 10 $\mu$g/ml, we enriched and purified strains resistant to 2; 2.5; 3; 4; 5; 8 and 10 $\mu$g/ml of kanamycin.

(1.4) Detection of the amplification of gene $Km^R$ in type A strains

Gene amplification in a bacterial chromosome can be detected by the following technique: the chromosomal DNA extracted from a strain containing an amplified structure is restrictively hydrolyzed with an endonuclease which has a single cleavage site in the amplification unit (A.U.). This restriction produces, in addition to the various chromosomal segments, a segment corresponding to the amplification unit. If the degree of amplification is adequate, analysis of this restriction by agarose electrophoresis will enable a band to be visualized which does not exist in the chromosomal DNA extracted from the parent "unamplified" strain and which corresponds to the A.U.

This technique was used to detect the amplification of pHV457 in the chromosome of the various strains resistant to kanamycin. Their chromosomal DNA and that of strain A were extracted and then restrictively hydrolyzed with ClaI endonuclease. This enzyme possesses a single cleavage site in pHV457. The products of this restriction weight is identical to that of pHV457 and it hybridizes with pBR322 sequences. These results suggest that this band corresponds to pHV457. Its high intensity observed both by the technique of electrophores is and by that of hybridization shows that the amplified structure is composed of several copies of pHV457 arranged in direct repetition.

It was moreover verified, in two ways, that the total DNA extracted from the kanamycin-resistant strains did not contain any extra-chromosomal form: by agarose gel electrophoresis and by hybridization according to Southern's technique.

Figure 6:
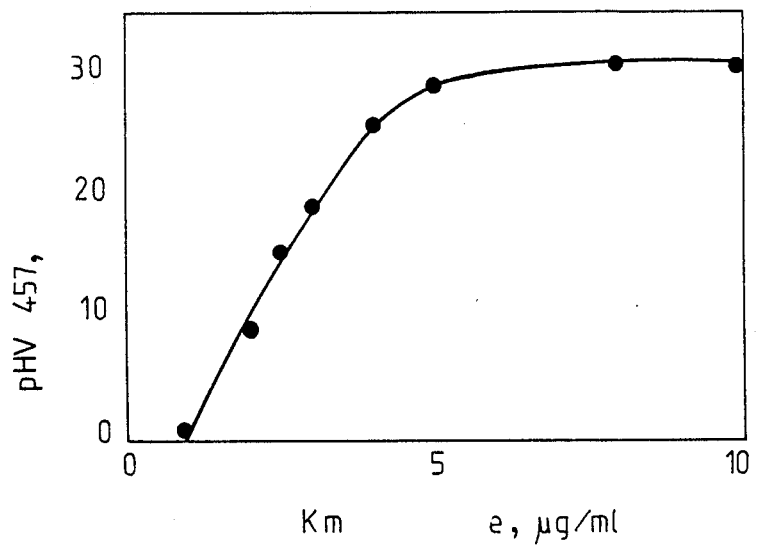
FIG. 6 shows the curve of the number of copies of the gene/resistance to kanamycin.

(1.5) Determination of the number of amplification units/chromosome in the kanamycin-resistant strains To determine the degree of amplification (number of A.U./chromosome) in these strains, their DNA restrictively hydrolyzed with ClaI and the chromosomal DNA of strain A, mixed or otherwise with a known quantity of linearized pHV457, were analyzed by agarose gel electrophoresis. By using densitometry to compare the intensity of the band observed in the DNA of these various strains with that observed with a known quantity of pHV457, the number of A.U./chromosome that they contain was determined. The results are shown in FIG. 6. From 2 to 5 $\mu$g/ml of kanamycin, the number of A.U./chromosome increases in proportion to the concentration of the antibiotic. At 2 $\mu$g/ml of kanamycin, the bacteria contain 7 copies of pHV457 per chromosome, and from 5 $\mu$g/ml they contain 30 copies. The overall extent of the amplification is equivalent to approximately 5% of the bacterial genome, assuming that the molecular weight of the chromosome is $2.5\times 10^9$ D, that of pHV457 being $4\times 10^6$ D $(30\times 4\times 10^6/2.5\times 10^9 = 0.05)$.

(1.6) Increase in the degree of amplification

Two approaches were used to attempt to isolate bacteria having a higher degree of amplification:

(a) production of bacteria hyper-resistant to kanamycin (resistant to kanamycin concentrations greater than 10 $\mu$g/ml);

(b) production of bacteria resistant to amikacin (Amk).

In fact, tests on growth inhibition around a disc of antibiotic showed that strain A $Km^R{}_{10}$ was more sensitive to amikacin than to kanamycin.

The strains resistant to 10 to 320 $\mu$g/ml of kanamycin all contain approximately 30 A.U./chromosome.

These results show:

that there are no bacteria which have greater degrees of amplification, or that kanamycin does not permit their selection;

that the hyper-resistance is not linked to an increase in the degree of amplification of the $Km^R$ gene.

Bacteria resistant to amikacin

By plating a culture of strain A $Km^R{}_{10}$ on a solid medium containing increasing concentrations of amikacin, it was observed that its plating efficiency was 50% on a solid medium containing 2.5 $\mu$g/ml of amikacin. To obtain bacteria resistant to concentrations of amikacin greater than 2.5 $\mu$g/ml, strain A $Km^R{}_{10}$ was seeded in liquid medium containing increasing concentrations of amikacin, and successive cycles were carried out. Strains resistant to 4; 8; 16; 32 and 64 $\mu$g/ml of amikacin (strains $AmK^R{}_4$ to $AmK^R{}_{64}$) were thereby isolated. Their DNA was extracted and restrictively hydrolyzed by ClaI.

The isolation of strains resistant to amikacin (up to 64 $\mu$g/ml) and analysis of the DNA of these strains show that the strains contain approximately 50 A.U./ chromosome, the overall extent of the amplification being equivalent to 7.5% of the bacterial chromosome.

Amikacin therefore enables bacteria to be selected which have a degree of amplification greater than those obtained with kanamycin. As with kanamycin, it is possible to isolate strains resistant to increasing concentrations of amikacin, although their degree of amplification remains constant. This limitation on the degree of amplification can be explained on the supposition that bacteria containing more than 50 A.U./chromosome do not exist, or that amikacin does not permit their selection.

(1.7) Activity of 4'-adenosylnucleotidyltransferase (4'ANT)

4'-Adenosylnucleotidyltransferase is an enzyme encoded by the pUB110 gene for resistance to kanamycin.

The activity of this enzyme was measured in crude extracts of strain A and of various strains resistant to subinhibitory concentrations of kanamycin.

Figure 7:
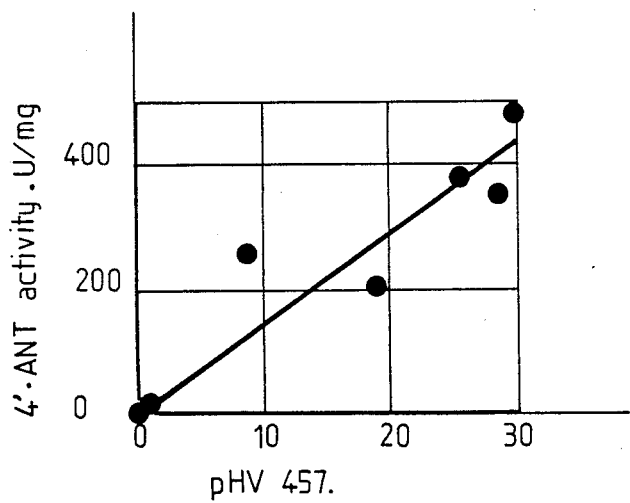
FIG. 7 shows the curve of the number of copies of the gene/4' ANT activity.

The results obtained (FIG. 7) show that this activity increases in proportion to the number of genes present in the bacterium, with a slope in the region of 1. This shows that each copy of the gene for resistance to kanamycin contributes in the same manner to the production of 4'ANT. The activity of this enzyme was also measured in crude extracts of the strains hyper-resistant to kanamycin (concentration > 10 µg/ml). The 4'ANT activity which they contain is identical to that present in strain A $Km^R{}_8$.

These results taken in combination show that the phenotype of hyper-resistance of these strains is not due to an increase in 4'ANT activity, nor to the increase in the degree of amplification. Other phenomena are responsible.

(1.8) Stability of the amplified structure in A $Km^R{}_{10}$ (30 A.U./chromosome)

To study the stability of the amplified structure, $10^{10}$ cells from a fresh culture of strain A $Km^R{}_{10}$ were seeded in liquid medium (100 ml) without antibiotic. After 3 generations, a 2nd cycle of culture in non-selective medium was seeded with $10^8$ cells. 5 successive culturings of this type, equivalent to 16 cell generations, were carried out. At the end of each culturing, aliquots were withdrawn and plated on solid medium containing 0 or 7.5 µg/ml of kanamycin. The quantity of viable bacteria and bacteria resistant to 7.5 µg/ml of kanamycin present in these cultures was determined by counting (for each measurement, approximately 1,000 colonies were counted).

After 16 generations in non-selective medium, the proportion of $Km^R{}_{7.5}$ bacteria is greater than 90% (this value is the limit of reliability of the counts). Since the plating efficiencies of the A strains having 30, 20 or 15 copies of pHV457 are 100, 25 and 0.1%, respectively, on a medium containing 7.5 µg/ml of kanamycin, it may be concluded that the bacteria from the 16 generations performed in non-selective medium have retained on average more than 20 A.U./chromosome.

Furthermore, it has been calculated that the probability of losing the $Km^R{}_{7.5}$ phenotype/generation is $<5\times 10^{-4}$. In addition, the chromosomal DNA of the bacteria from 5 generations performed in non-selective medium was extracted and their degree of amplification was measured by densitometry. These bacteria contained approximately 30 A.U./chromosome in one case and 28 A.U./chromosome in the other. The analysis of phenotypes and biochemical analysis hence shows that the amplified structure had high stability.

(2) Study of the amplification of the gene for resistance to kanamycin in strains B and C The structure present in strain A permits amplification of the gene for resistance to kanamycin. Is this amplification caused by special properties of the pBR322 sequences or by the existence of duplication? These two hypoteses were tested by studying the amplification of the gene for resistance to kanamycin:

when it is flanked by two identical sequences other than those of pBR322;

when it is not enclosed by duplicated sequences.

(2.1) Construction of strains B and C

These strains were constructed by inserting in the *B. subtilis* chromosome an integrating vector, either by a Campbell type mechanism requiring a single recombination event between the circular vector and the chromosome, or by a double recombination event between the linear vector and the chromosome (Niaudet et al., 1982).

Figure 8:
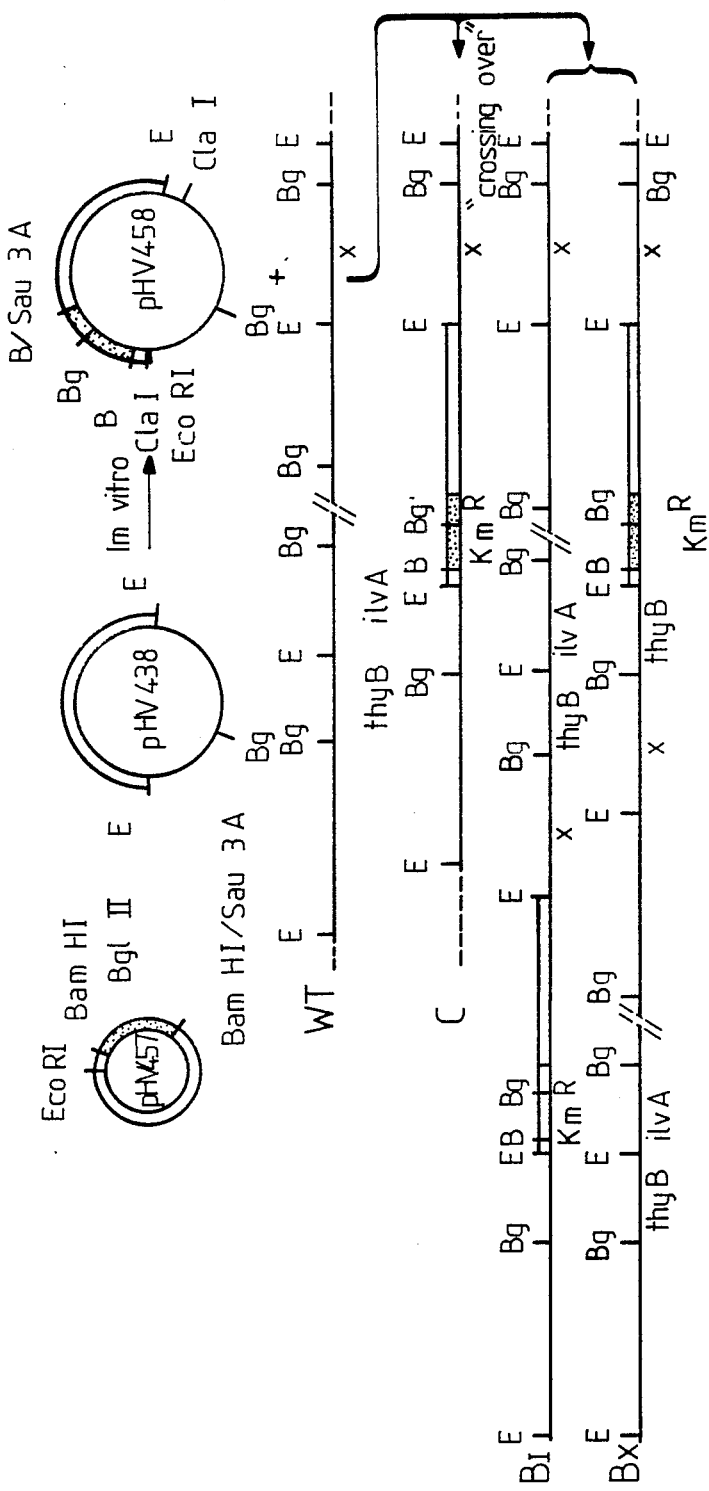
FIG. 8 shows the construction and structure of strains Bt, Bx and C.

The integrating vector used is pHV458. It is composed of pHV457 and two chromosomal segments Thy B and X (2 kb and 3.3 kb, respectively) originating from pHV438 (Niaudet et al., 1982) (FIG. 8). The vector is non-replicating in *B. subtilis* and contains the pUB110 gene for resistance to kanamycin. By means of these two chromosomal segments, it can be integrated in the *B. subtilis* chromosome in two ways:

(a) By a Campbell type mechanism in the Thy B or X regions, creating a duplication of the segment corresponding to the integration site around the gene for resistance to kanamycin. The two strains thereby constructed will be referred to as strain Bt and Bx (FIG. 8).

(b) By a double recombination event causing deletion of the chromosomal segment carrying the ilvA gene located between the Thy B and X regions, this segment being replaced by pHV457 (FIG. 8). The strain thereby constructed will be referred to as strain C.

Since it is impossible to select directly the integration of a single copy of the gene for resistance to kanamycin in the *B. subtilis* chromosome, to construct these three strains, competent cells of strain SB202 (Trp−) were transformed by pHV458 in congression with the chromosomal DNA of strain HVS246 (Trp+). Among the Trp+ transformants obtained, 10% of $Km^R$ clones were detected, 75% of which were Ile+ and 25% Ile−.

(2.1.1) $Km^R$ Ile− transformants (strain C)

To verify that these transformants had a type C structure (FIG. 8), the chromosomal DNA was extracted from two $Km^R$ Ile− transformants. After restrictive hydrolysis with EcoRI or BglII, the DNA was analyzed according to Southern's technique, using pHV458 as a probe.

The results obtained after autoradiography correspond to those expected from the integration of a pHV458 monomer in the Thy B-X region of the *B. subtilis* chromosome by a double recombination event. It has been possible to confirm this result by demonstrating, on the one hand that these transformants contain a region of homology with the pBR322 sequences, and on the other hand that they have lost the ilvA gene.

(2.1.2) $Km^R$ Ile+ transformants (strains Bt and Bx)

Six $Km^R$ Ile+ transformants were analyzed by Southern's hybridization technique. Their chromosomal DNA was extracted and then, after restrictive hydrolysis with EcoRI or BglII, hybridized with pHV458. The results obtained show that four transformants contain a pHV458 monomer integrated in their chromosome by a Campbell type mechanism, while the two others, containing several copies of pHV458, originate from the integration of a polymer of pHV458 in the *B. subtilis* chromosome.

The results obtained above did not enable the pHV458 integration site in the chromosome of strain SB202 (Thy B or X) to be known. To determine this, chromosomal DNA of the transformants containing a monomer of pHV458, as well as that of strain C, were restrictively hydrolyzed by the endonuclease BamHI. This enzyme recognizes a single site in pHV458 (FIG. 8). These restriction-cut DNA samples were then hybridized with pHV458 according to Southern's technique. The DNA of strain C possessed a hybridization band corresponding to a segment of approximately 6 kb. However, restrictive hydrolysis of the chromosomal DNA of strain C by BamHI produces two segments which can be hybridized with pHV458 (FIG. 8), the size of which depends on the position of the next BamHI sites in the chromosomal DNA. It follows from this that the size of the segment containing the thyB gene must be greater than 2.4 kb, while that corresponding to X must be greater than 9 kb. The 6 kb segment detected by hybridization hence corresponds to that containing the thyB gene, the other containing the segment X, the size of which is greater than 9 kb, not having been detected, probably because it was too large to be effectively transferred onto the nitrocellulose filter. The DNA of 2 of the 4 transformants containing a monomer of pHV458 show a band similar to that observed in strain C. Analysis of the structures expected for strains Bt and Bx (FIG. 8) shows that only DNA containing a structure of type Bt can generate this band.

The two transformants which have a 6 kb band in common with strain C hence originate from the integration of pHV458 by a Campbell type mechanism in the ThyB chromosomal region. The strain thereby constructed hence contains a duplication of the ThyB segments enclosing the gene for resistance to kanamycin (strain Bt). The other 2 transformants originate from the integration of pHV458 in the X chromosomal region. The strains contain a duplication of the X segments enclosing the gene for resistance to kanamycin (strain Bx) (FIG. 8). As with strains A and C, these two strains (Bt and Bx) have never been in direct contact with kanamycin.

(2.2) Amplification in the B strains

(2.2.1) Detection of bacteria of type B resistant to subinhibitory concentrations of kanamycin Aliquots of cultures of strains Bt and Bx were plated on solid media containing increasing concentrations of kanamycin to determine their plating efficiency on different concentrations. The results demonstrate:

(a) that strain Bx behaves like strain A, it withstands kanamycin at 1 µg/ml and contains bacteria capable of withstanding subinhibitory concentrations of kanamycin (2 to 8 µg/ml); the frequency of these bacteria varies from $10^{-4}$ to $10^{-6}$;

(b) strain Bt is more resistant to kanamycin than strains A and Bx, since its plating efficiency on 2 µg/ml of kanamycin is $5 \times 10^{-1}$ (instead of $10^{-4}$), and it also contains bacteria capable of growing on 4, 8 and 16 µg/ml of kanamycin. It is possible that the high resistance of this strain to kanamycin originates from an increased transcription of the $Km^R$ gene caused by a promoter of chromosomal origin.

(2.2.2) Enrichment of bacteria resistant to 10 µg/ml of kanamycin

To enrich the bacteria resistant to 10 µg/ml of kanamycin, the strains Bt and Bx were cultivated in liquid medium containing 10 µg/ml of kanamycin, as with strain A.

As with strain A, it was possible to demonstrate an enrichment of a subpopulation resistant to kanamycin in a culture of strain Bx in selective medium. In nonselective medium, this subpopulation is not enriched.

(2.2.3) Production of bacteria of type Bx hyper-resistant to kanamycin

By means of successive cycles in liquid medium containing increasing concentrations of kanamycin, strains derived from strain Bx, resistant to from 10 µg/ml to 0.1 g/ml of kanamycin were obtained.

(2.2.4) Determination of the degree of amplification of strains of type B

The number of copies of pHV458 present in the Bx strains resistant to from 10 µg to 20 mg/ml of kanamycin was determined by densitometry. These strains all contain approximately 20 A.U./chromosome.

As with strain A, the increase in the kanamycinresistance of the strains of type Bx is not associated with the increase in their degree of amplification. The hyper-resistance of these strains is hence caused by phenomena other than genetic amplification.

We have shown by densitometry that the strain of type Bt resistant to 10 µg/ml of kanamycin contained approximately 5 A.U./chromosome. It is assumed that the use of kanamycin as selective agent cannot permit isolation of strains of type Bt having a greater degree of amplification since the strains of type A and Bx resistant to 10 µg/ml of kanamycin contain a maximal degree of amplification.

The low degree of amplification of strain Bt $Km^R{}_{10}$ can probably be explained by assuming that the promoter of chromosomal origin which causes the overexpression of this gene is present in the amplification unit. Knowing that the gene for resistance to kanamycin is orientated in the direction of the small segment BglII—BamHI of pHV457 (J. E. Davis, personal communication) and knowing the structures of strains A, Bt and Bx, as well as their degree of resistance to kanamycin, it may be concluded that this promoter of chromosomal origin is located in the Thy B segment.

(2.2.5) Stability of the amplified structure in strain $Bx^R{}_{10}$ (20 A.U./chromosome)

The stability of the amplified structure was studied in strain $B \times Km^R{}_{10}$ in the same manner as with strain A $Km^R{}_{10}$.

The stability of the amplified structure in strain $B \times Km^R{}_{10}$ (20 A.U./chromosome) is similar to that observed in strain A $Km^R{}_{10}$. The probability that a $Km^R{}_{7.5}$ cell becomes $Km^s{}_{7.5}$ by generation is also $< 6 \times 10^{-4}$.

Since the stability of the amplified structure in strain Bx is identical to that present in strain A $Km^R{}_{10}$, it may be concluded that the chromosomal region deleted in strain A, but present in strain Bx, does not contain special functions capable of modifying the stability of the amplified structure.

(2.3) Strain C

(2.3.1) Production of strains of type C hyperresistant to kanamycin, and determination of their degree of amplification Starting from strain C, resistant to 1 µg/ml of kanamycin, strains were obtained resistant to 10–20 . . . 320 µg/ml of kanamycin. No amplification of the gene for resistance to kanamycin was detected in these strains. These results suggest that, in strain C, there is no subpopulation containing an amplified structure. It hence appears that a duplication around this gene is essential for it to be capable of being amplified. The hyperresistance of the strains of type C obtained above is thought to be caused by a modification in the sensitivity of the strain towards kanamycin.

(3) STUDY OF THE AMPLIFICATION OF THE GENE FOR RESISTANCE TO CHLORAMPHENICOL (CM) IN STRAINS α AND D

The studies performed with the strains of types A, Bx, Bt and C show that the gene for resistance to kanamycin can be amplified only if it is inserted between two identical sequences. To generalize these observations and show that the observed amplification is not due to special properties of the DNA fragment containing the gene for resistance to kanamycin, the amplification of the gene for resistance to chloramphenicol was studied when enclosed or otherwise by identical sequences.

(3.1) Constructions

(3.1.1) Strain α

The construction of strain α is described in paragraph (1.1.a). This strain contains in its chromosome sequences derived from pBR322 carrying the pC194 gene for resistance to chloramphenicol (pHV33Δ 81) not enclosed by identical sequences (FIG. 4).

(3.1.2) Strain D

In the chromosome of strain D, there is a duplication identical to that present in strain A (duplication of sequences derived from pBR322) enclosing the pC194 gene for resistance to chloramphenicol. To construct this strain, competent cells of strain C were transformed by a non-replicating plasmid in B. subtilis, pHV33Δ 81 (Dagert et al., 1983).

The preparation of plasmid pHV33Δ 81 was highly polymerized in order to avoid the integration of polymers of pHV33Δ 81 in the chromosome of strain C, and competent cells of this strain were transformed by DNA of the plasmid preparation of pHV33Δ 81 previously linearized by PstI. Thus linearized, this plasmid retains a part of its transforming power, since the cleavage which it bears can be repaired by interactions between the linearized plasmid and the homologous sequences present in the receptor cell (Contente and Dubnau, 1979). $2 \times 10^3$ $Cm^R$ transformants/µg of DNA were obtained. The total DNA extracted from a transformant, cleaved by EcoRI and BglII, was hybridized with pHV457. Its structure corresponded to that of the strain D sought (FIG. 9).

(3.2) Amplification of the gene for resistance to chloramphenicol

(3.2.1) Strain D

From successive cultures of strain D (resistant to 5 µg/ml of chloramphenicol) performed in liquid medium containing increasing concentrations of chloramphenicol, strains resistant to from 10 to 50 µg/ml of chloramphenicol were obtained. From a culture of strain D, it is possible to isolate the strains which have different degrees of amplification, and contain 2.5 and 7 A.U./chromosome. The amplification of the gene for resistance to kanamycin observed in strains A, Bx and Bt is hence not due to special properties of the sequences carrying the $Km^R$ gene.

Under the experimental conditions, it was hence not possible to isolate strains containing more than 7 A.U./chromosome. Two hypotheses can explain this result: either chloramphenicol does not permit their selection, or they do not exist.

(3.2.2) Strain α

Strain α withstands 5 µg/ml of chloramphenicol. From this strain, it was not possible to obtain bacteria resistant to concentrations of chloramphenicol greater than 5 µg/ml. The total DNA of the strain resistant to 5 µg/ml of chloramphenicol was extracted and analyzed by densitometry. No amplified structure was detected.

These studies performed on strains D and α demonstrate that the gene for resistance to chloramphenicol can be amplified if it is inserted between two identical sequences.

(4) CO-AMPLIFICATION OF TWO GENES

To demonstrate that it is possible to co-amplify the two genes, strain E was constructed. In its chromosome there were inserted pHV33Δ 81, which contains the gene for resistance to chlroamphenicol, and pHV458, which contains the gene for resistance to kanamycin. These two plasmids enclosed by two sequences X form A.U. No. 2 (FIG. 10). With this structure, the amplification of pHV458 necessarily brings about that of pHV33Δ 81. Strain E also contains a duplication of the pBR322 sequences enclosing the gene for resistance to chloramphenicol, pHV33Δ 81 forming A.U. No. 1 (FIG. 10). The amplification of pHV33Δ 81 can be independent of that of pHV458.

(4.1) Construction of strain E

Competent cells of strain Bx were transformed for resistance to chloramphenicol by plasmid pHV33Δ 81 previously linearized by PstI (see paragraph 3.1.2). $10^2$ transformants/µg of DNA resistant to 3 µg/ml of chloramphenicol were obtained. A clone was chosen, which was assumed to contain the structure shown in FIG. 10.

(4.2) Amplification of pHV458 and pHV33Δ 81

The cells of strain E were seeded in liquid medium containing 10 µg/ml of kanamycin or increasing concentrations of chloramphelcol (from 0 to 40 µg/ml). After 18 hours of incubation, the proportion of cells resistant to 10 µg/ml of kanamycin and 25 µg/ml of chloramphenicol were determined by plating on solid medium.

At the end of a culturing of strain E in non-selective medium, the proportion of cells resistant to 10 μg/ml of kanamycin is $2.5 \times 10^{-5}$ (value close to those determined for strains A and Bx). The proportion of cells resistant to 25 μg/ml of chloramphenicol is $3.3 \times 10^{-6}$. As expected, the bacteria resistant to 10 μg/ml of kanamycin were enriched during culturing in liquid medium containing 10 μg/ml of kanamycin (plating efficiency of 1 on $Km_{10}$ solid medium). This enrichment is accompanied by an increase in the quantity of bacteria resistant to 25 μg/ml of chloramphenicol, the plating efficiency being 0.1 on $Cm_{25}$ solid medium. The non-induction of the gene for resistance to chloramphenicol during culturing in the presence of 10 μg/ml of kanamycin must be the cause of the lower plating efficiency on $Cm_{25}$ than on $Km_{10}$ (1/10).

These results show that the amplification of one gene ($Km^R$ gene) brings about that of another gene ($Cm^R$ gene) present in the same amplification unit.

For the culturing performed in the low concentrations of chloramphenicol (up to 15 μg/ml), the co-amplification of the genes for resistance to chloramphenicol and to kanamycin appears small. This can be due either to an independent amplification of pHV33Δ81 (it forms part of A.U. No. 1 [FIG. 10]), or to insufficient co-amplication of the gene for resistance to kanamycin (the degree of amplification would be too low to confer resistance to 10 μg/ml of kanamycin). It is interesting to note that at chloramphenicol concentrations greater than 15 μg/ml, enrichment of the bacteria resistant to chloramphenicol is accompanied by that of bacteria resistant to 10 μg/ml of kanamycin (the proportion of $Km^R 10$ cells relative to $Cm^R 25$ cells increases from 50% to 90%). This shows that the amplification of A.U. No. 2 takes place preferentially to that of A.U. No. 1 alone.

The characteristics and origins of the strains and plasmids used in the examples of embodiment will be summarized in the tables below.

| BACTERIAL STRAINS | GENETIC MARKERS | ORIGIN |
|---|---|---|
| E. coli | | |
| HVC4S | thrA1 leu-8 thi-1 lacY1 tonA21 supE44 hadR rpeL | R. Davis |
| B. subtilis | | |
| SB202 | trpC2 tyrA1 aroB2 hisH2 | P. Schaeffer |
| a | (a) trpC2 tyrA1 aroB2 hisH2 ins [pHV452] del [ilvA2] | this work |
| A | (a) tyrA1 aroB2 hisH2 ins [pHV452] del [ilvA2] ins [pHV457] dup [pBR322Δ81] | this work |
| BT | (a) tyrA1 aroB2 hisH2 ins [pHV458, ThyB] dup [ThyB] dup [X] | this work |
| BX | (a) tyrA1 aroB2 hisH2 ins [pHV458, X] dup [X] dup [ThyB] | this work |
| C | (a) tyrA1 aroB2 hisH2 ins [pHV458] del [ilvA2] | this work |
| D | (a) tyrA1 aroB2 hisH2 ins [pHV458] del [ilvA2] ins [pHV33Δ81] dup [pBR322Δ81] | this work |
| E | (a) tyrA1 aroB2 hisH2 ins [pHV458, X] dup [X] dup [ThyB] ins [pHV33Δ81] dup [pBR322Δ81] | this work |

(a) genetic modifications due to insertions of plasmids in the chromosome of B. subtilis:
(1) ins followed by the name of a plasmid in square brackets signifies that the plasmid is inserted in the chromosome
(2) del or dup followed by the name of a gene, sequence or name of a plasmid signifies that after the insertion of the plasmid there has been deletion or duplication, respectively, of this gene, sequence or plasmid.
(3) When a plasmid can be inserted in several sites, its integration site is shown after the name of the plasmid.

| PLASMIDS | CONSTRUCTION | REFERENCE |
|---|---|---|
| pBR322 | cloning vector | Bolivar et al., 1977 |
| pC194 | natural isolate | Iordanescu, 1975 |
| pUB110 | natural isolate | Gryczan et al., 1978 |
| pHV32 | $Tc^R$ revertant obtained in vivo from pHV33 | Primrose and Ehrlich, 1981 |
| pHV33 | hybrid between pC194 and pBR322 | Primrose and Ehrlich, 1981 |
| pHV33Δ81 | PHV33 cut by BamHI eroded by BAL31 | Dagert et al., 1984 |
| pHV438 | hybrid between pHV32 and the ThyB and X segments of the B. subtilis chromosome | Niaudet et al., 1982 |
| pHV452 | hybrid between pHV33Δ81 and the ThyB and X sequences of the B. subtilis chromosome | this work |
| pHV457 | pUB110 segments Sau3A I and IV inserted in BamH1 site of pBR322 | this work |
| pHV458 | hybrid between pHV 457 and the ThyB and X segments of the B. subtilis chromosome | this work |

REFERENCES

Barat M., Anagnostopoulos C. and Schneider A. M. (1965) J. Bacteriol. 90:351-369

Campbell A. (1962) Advances Genet. 11:101-145

Contente S. and Dubnau D. (1979) Plasmid 2:555-571

Dagert M., Jones I. M., Goze A., Romac S., Niaudet B. and Ehrlich S. D. (1984) EMBO J. 3:81-86

Gryczan T. J. and Dubnau D. (1978) Proc. Natl. Acad. Sci. U.S.A. 75:1428-1432

Haldenwang S. Banner C. D. B., Ollington J. F., Losick R., Hoch J. A., O'Connor M. B. and Sonensheim B. L. (1980) J. Bacteriol. 142:90-98

Harris-Warwick R. M. and Lederberg J. (1977) J. Bacteriol. 133:1246-1253

Iordanescu S. (1975) J. Bacteriol. 124:597-601

Michel B., Niaudet B. and Ehrlich S. D. (1982) EMBO J. 1:1565-1571

Michel B., Niaudet B. and Ehrlich S. D. (1983) Plasmid 10:1-10

Niaudet B., Goze A. and Ehrlich S. D. (1982) Gene 19:277-284

We claim:

1. Process for preparing a strain of Bacillus, in the chromosome of which a specific gene has been amplified, said process comprising:
   (a) integrating at least one plasmid integration vector bearing said specific gene into the Bacillus chromosome, said chromosome now comprising:

(1) at least one heterologous DNA sequence which is an amplifiable unit, which comprises said specific gene, the expression elements of said gene and two identical sequences, wherein said sequences are tandemly duplicated; and (2) an amplifiable unit which also codes for a selectable gene; and (b) selecting by culturing the strains of Bacillus obtained on a selection medium corresponding to the selectable gene; and (c) isolating the strains which have the phenotype corresponding to the presence of an increased number of copies of said specific gene relative to the bacterial population before selection step (b).

2. Process as claimed in claim 1, wherein the selectable gene is a gene for resistance to a chemical compound and, at the stage (b), the strains are selected which have the highest resistance to this chemical compound.

3. Process as claimed in claim 2, wherein the chemical compound is an antibiotic.

4. Process as claimed in claim 3, wherein the selectable gene is the Km resistance or Cm resistance gene.

5. Process as claimed in claim 1, wherein the identical sequences known as duplicated sequences originate from a bacterial plasmid.

6. Process as claimed in claim 5, wherein the duplicated sequences originate from pBR322.

7. Process as claimed in claim 1, wherein the identical sequences consist of part of a DNA sequence of the wild type *B. subtilis* chromosome.

8. Process as claimed in claim 5, wherein the duplicated sequences consist essentially of the thy B gene.

9. Process as claimed in claim 1, wherein, in stage (a), the plasmid integration vector contains at least:
one amplification unit consisting of a duplicated sequence, of a selectable gene and of a specific gene, the Bacillus chromosome containing a duplicated sequence before the integration.

10. Process as claimed in claim 9, wherein the duplicated sequence present in the Bacillus chromosome has been introduced by integration by means of a plasmid integration vector.

11. Process as claimed in claim 1, wherein said specific gene is a foreign gene to naturally occurring Bacillus organisms.

12. Strain of Bacillus obtained by carrying out the process as claimed in claim 11.

13. Strain as claimed in claim 12, which strain is *B. subtilis*.

14. A process for preparing increased quantities of a specific protein per bacterial cell, wherein a strain according to claim 13, in which the specific gene codes for the said protein, is cultured in a culture medium, and the protein expressed is then separated.

15. A process for preparing increased quantities of a specific protein per bacterial cell, wherein a strain according to claim 12, in which the specific gene codes for the said protein, is cultured in a culture medium, and the protein expressed is then separated.

16. Process as claimed in claim 2, where the duplicated sequence consists essentially of a DNA sequence of the wild type *B. subtilis* chromosome.

17. Process as claimed in claim 2, wherein, in stage (a), the plasmid integration vector contains at least:
one amplification unit consisting of a duplicated sequence of a selectable gene and of a specific gene, the Bacillus chromosome containing a duplicated sequence before the integration.

18. Strain of Bacillus obtained by carrying out the process as claimed in claim 2.

19. Process as claimed in claim 2, wherein the identical sequences known as duplicated sequences originate from a bacterial plasmid.

20. Process as claimed in claim 3, wherein the identical sequences known as duplicated sequences originate from a bacterial plasmid.

21. Strain of Bacillus obtained by carrying out the process as claimed in claim 3.

22. Process for preparing a strain of Bacillus, in the chromosome of which a specific gene has been amplified, comprising the steps of:
(a) integrating at least one plasmid integration vector bearing said specific gene into a Bacillus chromosome, said chromosome having at least one amplifiable unit containing
(1) said specific gene,
(2) an expression element,
(3) a selectable gene, wherein the selectable gene is a gene for resistance to a chemical compound, and
(4) two identical sequences, wherein said sequences are tandemly duplicated;
(b) culturing said Bacillus on a selection medium corresponding to the selectable gene at a first concentration of said chemical compound;
(c) culturing said resistant Bacillus strain at increased concentration of said chemical compound thereby obtaining a more resistant Bacillus strain; and
(d) repeating step (c) until a highly resistant Bacillus strain is obtained;
whereby said chromosome of said highly resistant Bacillus strain contains an increased number of copies of said specific gene, said strain exhibiting a highly resistant phenotype as a result of the presence of an increased number of copies of said amplifiable unit.

* * * * *